United States Patent [19]
Pandit

[11] Patent Number: 5,836,970
[45] Date of Patent: Nov. 17, 1998

[54] HEMOSTATIC WOUND DRESSING

[75] Inventor: Abhay S. Pandit, Providence, R.I.

[73] Assignee: The Kendall Company, Mansfield, Mass.

[21] Appl. No.: 691,655

[22] Filed: Aug. 2, 1996

[51] Int. Cl.$^6$ .................................................. A61B 17/04
[52] U.S. Cl. ........................... 606/213; 606/151; 602/48; 602/49; 602/900
[58] Field of Search ............................... 606/213; 602/48, 602/49, 900

[56] References Cited

U.S. PATENT DOCUMENTS

| | | | |
|---|---|---|---|
| 4,956,350 | 9/1990 | Mosbey | 514/55 |
| 5,197,945 | 3/1993 | Cole et al. | 602/49 |
| 5,395,305 | 3/1995 | Koide et al. | 602/48 |
| 5,460,939 | 10/1995 | Hansbrough et al. | 435/240.1 |
| 5,587,175 | 12/1996 | Viegas et al. | 424/427 |

*Primary Examiner*—Gary Jackson
*Attorney, Agent, or Firm*—David J. Koris

[57] ABSTRACT

Wound dressings comprising a synergistic combination of reagents comprising a blend or mixture having effective amounts of chitosan and alginate to provide an absorption capacity for wound exudate far greater than that obtainable with the same amount by weight of either chitosan or alginate alone, along with the inherent hemostatic properties of the alginate and the other biological properties of the reagents including, but not limited to fungistic and bacteriostatic properties as well as the ability to accelerate wound healing by inducing high migration of poly- and mono-nuclear cells toward the wound and rapid granulating tissue formation with abundant angiogenesis. The alginate and chitosan may be provided in the form of a powder, film, gel, foam or mixtures thereof. In addition to the alginate and chitosan, the wound dressing may and frequently will contain other reagents providing specific desired functions. The dressing may be applied directly to the wound surface or carried on a suitable substrate applied to cover the wound.

20 Claims, No Drawings

HEMOSTATIC WOUND DRESSING

BACKGROUND OF THE INVENTION

This invention relates to wound dressings and, more particularly, to wound dressings having improved absorption capacity as well as possessing bacteriostatic and hemostatic properties.

The use of alginic material in wound dressings is well known in the art, both from the literature, including the patent literature, and from commercial use of these products in wound management.

As is well known, algin is a material obtained from seaweed. It can be converted into alginic acid which is insoluble and from which soluble salts such as sodium alginate or insoluble salts such as calcium alginate can then be obtained. Alginates are also readily available from pharmaceutical sources, most commonly as the salt form, e.g. sodium and/or calcium alginate.

As alluded to above, the use of calcium and sodium alginate materials in surgery and in the dressing of wounds has been known for many years, mainly in the form of gauze and the like. Commercial alginate products include, for example, CURASORB®, marketed by the Kendall Healthcare Products Company, division of The Kendall Company, assignee of this invention, SORBSON, marketed by Steriseal, A British company: KALTOSTAT and KALTOCARB, marketed by Britcair, another British company; and STOP HEMO, marketed by Windsor Laboratories, yet another UK company. The patent literature is also replete with references to alginate wound dressings. While not intended to represent an exhaustive search of the art, the following patents may nevertheless be taken as illustrative: U.S. Pat. Nos. 2,512,616; 3,879,168; 4,614,794; 4,837,024; 4,948,575; and, more recently, U.S. Pat. No. 5,470,576 assigned to the assignee of the present invention; British Patent Specifications 1,329,693; 1,394,742 and 2,221,620; and European Patent Application 87303252.8.

In general, it is well known in the art that ion exchange of some of the calcium with sodium ions present in the wound fluid provides a gel-like consistency which renders the dressing capable of absorbing appreciably greater amounts of wound fluid. The alginic materials as described in the aforementioned discussion of the state of the art are also well known for their hemostatic capabilities.

Chitosan, the partially deacetylated form of chitin, is another material known in the wound-management art for its hemostatic properties. It is a natural biopolymer composed of two common sugars, D-glucosamine and N-acetyl-D-glucosamine, both of which are constituents of the body. Chitin may be extracted from the outer shell of shrimps and crabs, isolated and then employed in the production of chitosan. In addition to its hemostatic properties, it possesses many other biological properties including bacteriostatic and fungistatic properties particularly useful for wound treatment. Chitosan has heretofore been employed in various physical forms for wound treatment, e.g. as a solution/gel; film/membrane; sponge; powder or fiber.

Like alginic materials previously mentioned, the literature is replete with references to chitosan in wound treatment, alone or in combination with other reagents. As illustrations of the patent literature mention may be made of the following: U.S. Pat. Nos. 3,632,754; 3,903,268; 4,394373; 4,532,134; 4,570,629; 4,572,906; 4,614,794; 4,651,725; 4,659,700; 4,699,135; 4,956,350; 5,395,305; and 5,420,197;

While hemostatic reagents such as alginates and chitosan have achieved commercial success in wound management, there yet remains the need for a dressing containing wound-friendly hemostatic reagents which will not only possess excellent absorption capacity for wound fluids, but will also provide bacteriostatic activity.

Stated simply, this need in the wound care art is the task of the present invention.

BRIEF DESCRIPTION OF THE INVENTION

In accordance with the present invention, this task has been solved in an elegant manner by the discovery that, unexpectedly, a blend or mixture of chitosan and alginate provides a synergistic combination which can provide an absorption capacity for wound exudate of on the order of 28 times its dry weight, as compared, for example, to an absorption capacity of alginate for wound exudate of 10–15 times its dry weight.

In a particularly preferred embodiment, collagen is included in the blend or mixture.

In still another preferred embodiment, the dressing will comprise a composite powder of maltodextrin/chitosan salt/alginate.

DETAILED DESCRIPTION OF THE INVENTION

As was heretofore mentioned, the present invention relates to wound management, the essence of the invention being providing a wound dressing comprising a blend or mixture comprising effective amounts of chitosan and alginate to provide an absorption capacity far greater than that obtainable with either reagent alone, along with the inherent hemostatic properties of the alginate and the other biological properties of the reagents including, but not limited to fungistic and bacteriostatic properties as well as the ability to accelerate wound healing by inducing high migration of poly- and mononuclear cells toward the wound and rapid granulating tissue formation with abundant angiogenesis.

The alginate and/or the chitosan may be provided in a blend or mixture in the form of a multilayer composite, a powder, a fiber, a film, a gel; or in a foam. Various combinations of these forms are also contemplated. The reagents may be applied directly to the wound surface or they may be adhered to a gauze vehicle or other substrate, e.g. a gel, hydrocolloid, foam, etc., to provide a bandage for application to the wound. In the latter case, they may be coated onto the substrate or adhesively secured thereto. In either case, the dressing may be in the form of an island dressing wherein the effective reagents are disposed substantially centrally on the bandage surface surrounded around their periphery by a layer of medical grade pressure-sensitive adhesive for securing the dressing to intact skin surrounding the wound.

As heretofore noted, the invention in its broadest form contemplates a wound dressing comprising effective amounts of chitosan and alginate. As used herein and in the appended claims, the term "effective amount" means and amount which will provide a synergistic combination, namely will provide an absorption capacity greater than that obtainable with a given dry weight of either chitosan or alginate alone.

The proportions by weight of chitosan to alginate which can constitute "effective amounts" may vary over a wide range and may, for example, be on the order of 5:1 to 1:5. Preferred are ratios by weight of 7:3 to 3:7 chitosan to alginate, a 1:1 ratio being particularly preferred.

The following procedures are illustrative of the physical forms of the dressings contemplated by this invention.

Chitosan/Alginate Fibers

The procedures for preparing the fibers contemplated by this invention are per se known in the art and accordingly need not be described in great detail.

Chitosan/alginate fibers may be obtained utilizing wet spinning techniques. Depending upon whether a mixture of chitosan and alginate fibers or a composite fiber containing both reagents is contemplated, a polymeric solution of chitosan and/or alginate (commonly referred to generically as the "spin dope") is inserted in a spin cylinder and pushed downward by a piston to extrude a liquid jet through a spinneret. [This may alternatively be accomplished by a screw extruder.] The liquid jet may be immersed directly into a coagulation bath or it can go through an inert gas gap first. The gas gap and coagulation bath are to solidify the fiber by setting up a skin through which the solvent inside the fiber can diffuse. From the coagulation bath, the fibers are wound up on rollers where they are given an initial draw. One or two additional baths may be employed for solvent removal and washing. They can also be used to provide additional fiber drawing under wet conditions. While the draw step is not necessary, it is preferred because better tensile properties generally result due to polymer chain alignment. Either or all baths may be heated if desired. The fibers are withdrawn from the final wash bath onto a take-up roll. They may be dried prior to being taken up on the roll or, alternatively, the take-up roll may then be taken to a drying tunnel where warm air may be applied to dry the roll.

The following examples illustrate the preparation of a non-woven fabric of chitosan and alginate fibers.

EXAMPLE 1

100.0 grams of chitosan chloride were mixed in 1.5 liters of water until blended. 200.0 grams of glycerol were blended into the mixture, after which 200.0 grams of polyethylene glycol ("PEG") were then added. The resulting mixture was then filtered and extruded through a spinneret into a coagulation bath of sodium hydroxide (pH=13). The resulting chitosan fibers were collected and centrifuged for one hour, dried in a dryer for 30 minutes and then dried at room temperature under tension onto a take-up roll to provide a roll of chitosan fibers. A similar solution of sodium alginate was then extruded through the spinneret into a coagulation bath of calcium chloride and dried to provide a roll of calcium alginate fibers. The alginate and chitosan fibers were then mixed while carding in known manner to provide a non-woven fabric containing on the order of a 1:1 ratio by weight of alginate: chitosan.

EXAMPLE 2

Example 1 was repeated, using 200 grams of glycerol in lieu of 200 grams of glycerol and 200 grams of PEG in the spin dope.

EXAMPLE 3

Example 1 was repeated, using 200 grams of PEG in lieu of 200 grams of glycerol and 200 grams of PEG in the spin dope.

EXAMPLE 4

Example 1 was repeated, except that no glycerol or PEG was added.

Chitosan/Alginate Film

In a similar manner, an aqueous solution of chitosan and alginate along with a plasticizer such as glycerol and/or PEG is formed. This solution is then cast onto trays to the desired thickness and then air-dried to form films of the desired thickness, e.g. 2 to 10 mils thick.

The following examples illustrate the preparation of chitosan/alginate films.

EXAMPLE 5

Into 1.5 liters of water were mixed 100 grams of chitosan chloride. 200 grams of PEG were then added. Next, 0.5 liter of water was added over the next 20 minutes, after which 200 grams of glycerol were slowly added, followed by 100 grams of sodium alginate and 400 milliliters of water. The resulting mixture was then spread onto trays and air dried. After about 48 hours a flexible chitosan/alginate film was formed.

EXAMPLE 6

Into about 1.5 liters of water at 50° C. slowly add 100 grams of chitosan chloride and 100 grams of sodium alginate. Slowly add additional water as needed to complete solution of the chitosan and alginate, then add 200 grams of glycerol and 200 grams of PEG. Spread on trays and air dry for 48 hours as in Example 4.

EXAMPLE 7

Example 5 repeated, except that only 200 grams of glycerol were added, deleting the addition of 200 grams of PEG also.

EXAMPLE 8

Example 6 was repeated, substituting 200 grams of PEG for the glycerol.

Films of chitosan alone and films containing equal parts of by weight of chitosan and alginate, as prepared in the foregoing examples, were compared for absorptive capacity. The test results are set forth in the following table.

TABLE 1

| FILM | DRY WT. (GMs) | 1 HR WT (GMS) | 4 HR WT (GMS) | 24 HR WT (GMS) | 48 HR WT (GMS) |
|---|---|---|---|---|---|
| CHITOSAN ALONE | 1.85 | 6.82 | 10.78 | 15.96 | [*] |
| CHITOSAN/ALGINATE | 1.73 | 10.18 | 17.14 | 26.09 | 28.49 |

*FILM DISSOLVED
n = 3

The foregoing data represents the mean of three tests (n=3). It establishes the clear superiority of chitosan/alginate film over the chitosan film alone in terms of absorptive capacity. Films of alginate alone were not prepared as they are not feasible for application in this form as they do not have a structural integrity.

Chitosan/Alginate Foam

To prepare the foam, chitosan and alginate are admixed with a minimal amount of solvent and then freeze dried.

The following Examples are illustrative.

EXAMPLE 9

Equal parts by weight of chitosan chloride and sodium alginate (50 grams of each) were dissolved in minimum amount of water by slowly adding water until solution. The eutectic point was noted and the product was then freeze dried to provide a chitosan/alginate foam.

EXAMPLE 10

33 grams each of chitosan chloride and sodium alginate were slowly dissolved in a minimal amount of water. 33 grams of glycerol were added for flexibility and the resulting mixture blended. The eutectic point was noted and the product freeze dried to form a foam. In the following further illustrative examples collagen was admixed with the chitosan and alginate to obtain a chitosan/alginate/collagen foam.

EXAMPLE 11

A 1% aqueous solution of acetic acid containing dispersed collagen, a 6.6% aqueous solution of chitosan chloride and a 11% aqueous solution of sodium alginate were mixed and homogenized at high shear to provide a solution containing the following proportions of ingredients by weight:

|  |  |
|---|---|
| Collagen | 90% |
| Chitosan | 05% |
| Alginate | 05% |

The resulting solution was degassed in vacuo and then freeze dried to provide the chitosan/alginate/collagen foam.

EXAMPLE 12

Example 11 was repeated, modifying the solution to contain the following proportions of ingredients by weight:

|  |  |
|---|---|
| Collagen | 80% |
| Chitosan | 10% |
| Alginate | 10% |

EXAMPLE 13

Example 11 was again repeated, modifying the solution to contain the following proportions of ingredients by weight:

|  |  |
|---|---|
| Collagen | 70% |
| Chitosan | 15% |
| Alginate | 15% |

Chitosan/Alginate Hydrocolloid

A water-swellable hydrocolloid was prepared containing equal parts of sodium alginate and chitosan chloride.

In the following four examples, wafers were prepared consisting of a medical grade pressure-sensitive acrylic adhesive incorporating the alginate/chitosan water-swellable hydrocolloid. The acrylic adhesives employed were characterized as being moist, gentle and 'wound friendly.' The water-absorbency and bacteriostatic activities of the wafers were compared with controls consisting of comparable products containing sodium alginate alone or chitosan chloride alone incorporated in the acrylic adhesive.

EXAMPLE 14

A wafer dressing was prepared about 40 mils thick containing the following parts by weight ("PBW") of ingredients

|  | PPW |
|---|---|
| Acrylic adhesive | 69 |
| Sodium Alginate | 15 |
| Chitosan Chloride | 15 |
| Antioxidant | 1 |

A 0.5 mil polyurethane film was then laminated over one side of the dressing to provide a water-impermeable barrier. A standard silicone release sheet was then applied over the opposed adhesive surface. The product was then sterilized.

EXAMPLE 15

Example 14 was repeated, except that the wafer dressing contained:

|  |  |
|---|---|
| Acrylic Adhesive | 79 |
| Sodium Alginate | 10 |
| Chitosan Chloride | 10 |
| Antioxidant | 1 |

EXAMPLE 16

Example 14 was repeated again, except that the wafer dressing contained:

|  |  |
|---|---|
| Acrylic Adhesive | 69 |
| Chitosan Chloride | 30 |
| Antioxidant | 1 |

EXAMPLE 17

Example 14 was repeated once more, except that the wafer dressing contained:

|  |  |
|---|---|
| Acrylic Adhesive | 69 |
| Sodium Alginate | 30 |
| Antioxidant | 1 |

The formulations of Examples 14 and 15 exhibited much higher absorbency and bacteriostatic activity than did the controls of Examples 16 and 17.

Chitosan/Alginate Powder

In the following Table, 100 grams of the following hydrophilic powders were prepared.

TABLE 2

| FORMULATION | CHITOSAN Cl | Na ALGINATE |
|---|---|---|
| 1 | 100 | 0 |
| 2 | 0 | 100 |
| 3 | 50 | 50 |

The absorbency in grams per gram of each formulation was determined at intervals of one minute, one hour, 4 hours, 24 hours, 28 hours and 96 hours. The results are recited in TABLE 3.

TABLE 3

| FORMU-LATION | 1 MIN | 1 HR | 4 HRS | 24 HRS | 28 HRS | 48 HR | 96 HRS |
|---|---|---|---|---|---|---|---|
| 1 | 2.0 | 7.5 | 10.0 | 7.5 | 6.0 | 3.5 | 1.0 |
| 2 | 3.2 | 5.0 | 7.0 | 5.0 | 4.0 | 3.0 | 1.0 |
| 3 | 2.2 | 5.4 | 8.0 | 14.0 | 15.0 | 18.0 | 26.5 |

From the test data shown in TABLE 3, it will thus be seen that the combination of chitosan and alginate provides a remarkable synergism in terms of the ability of equal weights of powder to absorb fluid, e.g. wound exudate. This result was not suggested by the prior art and therefore unexpected prior to the present invention. This is particularly true since, chitosan or alginate alone (formulations 1 and 2) disintegrated from their gel structures after 4 hours and, as noted from the TABLE, did not absorb any more fluids.

While similar data was not obtained prior to the filing of this application for other physical forms of chitosan/alginate, e.g. the other forms previously discussed, it is postulated that similar synergism will exist.

As was mentioned earlier, in a preferred embodiment of this invention, the powder blend will also contain maltodextrin, a biologically compatible wound-friendly polysaccharide possessing bacteriostatic properties and which is further useful as a filler in the contemplated wound dressing powders. Maltodextrin is a polysaccharide, constitutionally between dextrin and maltose, which may be produced from the starch in barley during the manufacture of malt. Its composition depends on the relative amounts of maltose and dextrin. It may further be described as a nutritive saccharide polymer consisting of D-glucose units linked primarily by α-1,4-bonds, having a dextrose equivalence less than 20. [As known, dextrose equivalence (DE) is a quantitative measure of the degree of starch polymer hydrolysis. It is a measure of reducing power compared to a dextrose standard of 100. The higher the DE, the greater the extent of starch hydrolysis.]

In accordance with the present invention, the maltodextrin to be employed in the wound dressing blend of powders will have a DE on the order of about 10 to about 19.

The remaining two components of the powder mixture, namely the chitosan and alginate will be present in equal parts (percentages) by weight, i.e. in a ratio by weight of 1:1, with the total by weight of all three components then being 100% by weight of the weight of the powder blend.

Powder blends of maltodextrin/chitosan chloride/sodium alginate were prepared as recited in the following table:

TABLE 4

| FORMULATION | MALTODEXTRIN | CHITOSAN CL | NA ALGINATE |
|---|---|---|---|
| 4 | 10 gms | 45 gms | 45 gms |
| 5 | 20 gms | 40 gms | 40 gms |
| 6 | 30 gms | 35 gms | 35 gms |
| 7 | 40 gms | 30 gms | 30 gms |
| 8 | 50 gms | 25 gms | 25 gms |
| 9 | 60 gms | 20 gms | 20 gms |
| 10 | 70 gms | 15 gms | 15 gms |
| 11 | 80 gms | 10 gms | 10 gms |
| 12 (control) | 100 gms | 0 | 0 |

As was done with the chitosan/alginate powders and reported in TABLE 3, the formulations of the powders recited in TABLE 4 were tested for absorbency in grams per each gram of the formulation at intervals of 4 hours, 24 hours, 28 hours, 48 hours and 96 hours.

The absorbency data is reported in the following table.

TABLE 5

| FORMULATION | 4 HRS | 24 HRS | 28 HRS | 48 HRS | 96 HRS |
|---|---|---|---|---|---|
| 4 (10/45/45) | 8.0 | 13.5 | 14.5 | 18.0 | 24.5 |
| 5. (20/40/40) | 7.0 | 13.0 | 14.0 | 19.0 | 24.5 |
| 6. (30/35/35) | 7.5 | 12.5 | 14.5 | 17.5 | 24.5 |
| 7. (40/20/20) | 7.0 | 13.0 | 13.5 | 18.5 | 21.0 |
| 8. (50/25/25) | 7.5 | 12.0 | 13.0 | 16.0 | 18.0 |
| 9. (60/20/20) | 7.0 | 10.0 | 11.0 | 14.0 | 18.0 |
| 10. (70/15/15) | 7.0 | 11.0 | 13.0 | 14.0 | 17.5 |
| 11. (80/10/10) | 6.0 | 9.0 | 9.0 | 10.0 | 12.5 |
| 12. (100/00/00) | 1.0 | 2.0 | 2.0 | 2.0 | 3.0 | n = 3

With reference back to the test data recited in TABLES 3 and 5, it will be appreciated by those familiar with such analytical data that a single run, as recited in these tables, does not necessarily recite precise or completely accurate and reproducible data. To do so, repeated runs providing mean figures and a standard deviation would be required. Nevertheless, they are entirely accurate as an indication of the results to be achieved.

With reference to TABLE 3, the synergistic results in terms of dramatic improvement in absorptive power are readily apparent. It doesn't make any difference in this context whether the absorption at 96 hours is 26× as great or some slightly greater or lesser number. What is also apparent is that with chitosan or alginate alone (Formulations 1 and 2, respectively, the absorptive capacity drops off in time meaning, for example, that for larger amounts of wound fluids, the dressing needs changing after, say, four hours.

As contrasted, and with reference to Formulation 3, it will be observed that the absorption is greater over the periods of time evaluated, namely increasing from 8.0 gms/gm of formulation in 4 hours to 26.5 gms/gm of formulation at 96 hours.

Turning now to TABLE 5, allowing for a slight margin of error in the experimental data, it will be observed that as the percentage of maltodextrin increases, the absorptive capacity decreases across the board at the time intervals measured. Stated another way, the less chitosan/alginate in the powder blend, the less absorptive capacity. This, of course, is to be anticipated. As seen from Formulation 13, included as a Control, it will be observed that maltodextrin alone does not exhibit great absorptive capacity, absorbing 1–3 times its weight over the period of time tested.

Yet, the entire range of proportions appearing in TABLE 5 establish an absorptive capacity which, while less than that provided by chitosan/alginate alone, is nevertheless very substantial while at the same time incorporating the above-mentioned advantages of the maltodextrin in the dressing. The data presented will provide all the information required for the skilled worker to make an informed decision as to what percentage of maltodextrin should be employed in the blend, which decision may even be a matter of individual whim.

As was previously mentioned, in another preferred embodiment of this invention, the dressing may also comprise a mixture or combination of chitosan, alginate and collagen.

As is well known, collagen is a major constituent of various structures rich in dense, connective tissue, e.g. dura mater, fiasco, intestine (catgut) or tail tendons. While it can be obtained by enzymatic digestion, non-enzymatic procedures are preferred because they are less expensive and do not disrupt the fibril structure of collagen.

Collagen films, membranes, tapes, sponges, and felts have heretofore been used for wound dressings, collagen sponges or foams, e.g. a highly crosslinked collagen sponge being particularly useful.

Irrespective of the form, it is known that collagen as a substrate favors cell growth, making, it particularly useful for wound and burn dressings.

As reported, for example, by Milos Chvapil in "*Collagen Sponge: Theory and Practice of Medical Applications*" appearing in *J. Biomed. Mater. Res.*, Vol. 11, pp. 721–741 (1977), collagens materials had several beneficial effects in dressings. A dressing of reconstituted collagen film afforded excellent protective coverage over large areas of excised skin or third degree burns for 3–4 weeks, exhibiting diminished fluid loss and helping to maintain sterility. In burn studies, the collagen was found equal to autogenous skin grafts in diminishing fluid loss maintaining sterility and promoting healing. In studies on treating pressure sores in paraplegic patients with collagen sponges, the clinicians noted the following: (1) wounds were clean and bacterial infection retarded; (2) drainage of wound secretion was diminished; (3) formulation of new granulation tissue was improved; (4) undermined edges of pressure sores were closed; (5) formation of the epithelium was stimulated; (6) closed wounds showed no contractures; (7) moist pressure ulcers which had showed no tendency to heal were closed; (8) no immunological reactions towards collagen were observed; and (9) the general condition of the patient was improved.

The patent literature is also replete with references to the use of collagen in wound dressings. Illustrative U.S. patents include U.S. Pat. No. 4,759,354 assigned to the assignee of the present invention and the following patents mentioned therein: U.S. Pat. Nos. 2,202,566; 3,471,598; 3,491,760; 3,800,792; 4,294,241; 4,438,258; and 4,570,629.

In view of the many known advantages of collagen in wound management, it will be appreciated that it will be most desirable to incorporate collagen into the chitosan/alginate dressings contemplated by this invention having exceptional absorptive capacity as well as hemostatic properties in order to include the known advantages of collagen in wound treatment.

The chitosan, alginate and collagen components of the dressings herein contemplated, like the embodiments of this invention previously discussed, may take various physical forms, e.g. as a fiber, powder, foam, film, or mixtures thereof By way of illustration, in one physical form that is envisioned, equal parts of each may be in fibrous form, either as composite fibers or a mixture of fibers.

In another embodiment, the dressing may comprise collagen and chitosan powders admixed with alginate fibers.

In still another embodiment, alginate and chitosan fibers may be incorporated in collagen foam, e.g. during freeze drying of collagen.

In yet another embodiment, chitosan powder and alginate fibers may be incorporated in collagen foam, e.g. during freeze drying of the collagen. In a further embodiment contemplated by this invention, collagen powder and alginate fiber may be incorporated into chitosan foam.

In a still further embodiment, collagen and alginate fibers may be incorporated into chitosan foam. Finally, it is contemplated that chitosan and alginate powders may be incorporated in equal proportions in collagen foam during freeze drying.

It will be appreciated that various other reagents providing specific desired functions may be included in the wound dressings herein contemplated. By way of illustration, mention may be made of growth factors, antibiotics, germicides, fungicides, plasticizers, preservatives, and the like.

It will be appreciated that the aforementioned effective reagents which is the essence of the novelty upon which patentability is here predicated may be applied to the wound in the various ways per se known in the art. They may be topically applied to the wound surface or packed into the wound followed by application of a protective gauze dressing or the like; or the effective ingredients may be incorporated into a suitable matrix or substrate for application to the wound, e.g. as a coating, impregnating the matrix, or by an adhesive.

The wound dressing containing the effective reagents of this invention may be of a per se known physical form for wound dressings. For instance, one useful form is as an island dressing wherein a backing or cover sheet, e.g. of a polymeric material which provides a barrier to bacteria contains a pressure-sensitive medical grade adhesive coating covering one surface thereof and a gauze or other suitable matrix containing the effective reagents of this invention is centrally disposed on the adhesive surface for application on the wound leaving free adhesive coating around the periphery of the matrix for adhering the dressing to healthy skin surrounding the wound.

Other forms of dressings will be readily suggested to those skilled in the art and their selection will be a matter of individual choice in the light of the foregoing description.

Since various changes may be made without departing from the scope of the invention herein contemplated, it is therefore to be expressly understood that the foregoing description is by way of illustration and not by way of limitation.

What is claimed is:

1. A wound dressing comprising a blend or mixture consisting of effective amounts of chitosan and alginate in a weight ratio within the range of about 5:1 to 1:5, wherein the chitosan and alginate are present in a form selected from the group consisting of a multilayered composite, a powder, a composite fiber, a film, a gel, a foam or a mixture thereof.

2. A wound dressing as defined in claim 1 wherein the blend or mixture further contains collagen.

3. A wound dressing as defined in claim 1 wherein the ratio by weight of chitosan to alginate is from about 5:1 to 1:5.

4. A wound dressing as defined in claim 1 wherein the dressing comprises a film.

5. A dressing as defined in claim 4 wherein the film is from about 2 to about 10 mils thick.

6. A dressing as defined in claim 1 wherein the dressing comprises a foam.

7. A dressing as defined in claim 6 wherein the foam further contains collagen.

8. A dressing as defined in claim 1 wherein the dressing comprises a powder.

9. A dressing as defined in claim 8 wherein the powder further contains maltodextrin.

10. A dressing as defined in claim 9 wherein the maltodextrin has a DE of from about 10 to about 19.

11. A dressing as defined in claim 10 wherein the ratio by weight of chitosan to alginate is 1:1.

12. A dressing as defined in claim 1 wherein the dressing further includes a growth factor, an antibiotic, a germicide, a fungicide, a plasticizer or a preservative.

13. A wound dressing comprising effective amounts of chitosan, alginate and collagen, wherein the physical forms of the chitosan, alginate and collagen are not all the same, and wherein the chitosan and alginate are present in a chitosan:alginate ratio of about 5:1 to about 1:5.

14. A wound dressing as defined in claim 13 wherein the dressing comprises collagen and chitosan powders admixed with alginate fibers.

15. A wound dressing as defined in claim 13 wherein the dressing comprises alginate and chitosan fibers incorporated in a collagen foam.

16. A wound dressing as defined in claim 13 wherein the dressing comprises chitosan powder and alginate fibers incorporated in a collagen foam.

17. A wound dressing as defined in claim 13 wherein the dressing comprises collagen and alginate fibers incorporated in a chitosan foam.

18. A wound dressing as defined in claim 13 wherein the dressing comprises chitosan and alginate powders incorporated in collagen foam.

19. A wound dressing comprising a non-woven fabric having a mixture of alginate fibers and chitosan fibers obtained by wet spinning techniques, in an alginate:chitosan weight ratio of about 5:1 to about 1:5.

20. The wound dressing as defined in claim 19, wherein said alginate:chitosan weight ratio is about 1:1.

* * * * *